(12) United States Patent
Siegal et al.

(10) Patent No.: US 9,044,334 B2
(45) Date of Patent: Jun. 2, 2015

(54) SPINAL SURGERY IMPLANTS AND DELIVERY SYSTEM

(75) Inventors: Tzony Siegal, Moshav Shoeva (IL); Dvir Keren, Tel Aviv (IL); Oded Loebl, Tel Mond (IL); Didier Toubia, Raanana (IL)

(73) Assignee: NLT SPINE LTD., Kfar Saba (IL)

( * ) Notice: Subject to any disclaimer, the term of this patent is extended or adjusted under 35 U.S.C. 154(b) by 0 days.

(21) Appl. No.: 13/146,014

(22) PCT Filed: Jul. 21, 2011

(86) PCT No.: PCT/IB2011/053268
§ 371 (c)(1),
(2), (4) Date: Jul. 24, 2011

(87) PCT Pub. No.: WO2012/011078
PCT Pub. Date: Jan. 26, 2012

(65) Prior Publication Data
US 2013/0110239 A1    May 2, 2013

Related U.S. Application Data

(60) Provisional application No. 61/366,166, filed on Jul. 21, 2010, provisional application No. 61/471,763, filed on Apr. 5, 2011.

(51) Int. Cl.
*A61F 2/44* (2006.01)
*A61B 17/70* (2006.01)
(Continued)

(52) U.S. Cl.
CPC .............. *A61F 2/442* (2013.01); *A61B 17/7098* (2013.01); *A61B 17/8852* (2013.01); *A61F 2/4455* (2013.01); *A61F 2/4465* (2013.01); *A61F 2/4611* (2013.01); *A61F 2002/2817* (2013.01); *A61F 2002/2835* (2013.01); *A61F 2002/302* (2013.01); *A61F 2002/30331* (2013.01); *A61F 2002/30367* (2013.01); *A61F 2002/30426* (2013.01);
(Continued)

(58) Field of Classification Search
USPC .................. 606/99, 86 A, 86 B, 914, 915; 623/17.11–17.16
See application file for complete search history.

(56) References Cited

U.S. PATENT DOCUMENTS 4,969,888 A * 11/1990 Scholten et al. ............... 606/94
6,096,038 A    8/2000 Michelson
(Continued)

FOREIGN PATENT DOCUMENTS

DE         19710392        7/1999
IL      WO2008084479       7/2008
(Continued)

*Primary Examiner* — Michael T Schaper
*Assistant Examiner* — Tracy Kamikawa
(74) *Attorney, Agent, or Firm* — Mark M. Friedman (57) ABSTRACT

A spinal surgery tool system including an elongated conduit and an implant is disclosed. The implant assumes a straight configuration within the elongated conduit and is deployable from the elongated conduit into a closed or nearly-closed loop configuration for deployment interposed between two tissue surfaces to define an enclosed volume. The conduit and the implant are configured such that, when the implant is deployed in the loop configuration, an opening formed in a proximal portion of the implant forms a contiguous channel with a passageway along the conduit so as to provide a continuous access channel along the elongated conduit into the enclosed volume.

10 Claims, 9 Drawing Sheets

(51) Int. Cl.
   *A61B 17/88*   (2006.01)
   *A61F 2/46*    (2006.01)
   *A61F 2/28*        (2006.01)
   *A61F 2/30*        (2006.01)

(52) U.S. Cl.
   CPC ............ *A61F 2002/30462* (2013.01); *A61F 2002/30471* (2013.01); *A61F 2002/30509* (2013.01); *A61F 2002/3052* (2013.01); *A61F 2002/30624* (2013.01); *A61F 2002/30632* (2013.01); *A61F 2002/30677* (2013.01); *A61F 2002/30777* (2013.01); *A61F 2002/30785* (2013.01); *A61F 2002/30792* (2013.01); *A61F 2002/30795* (2013.01); *A61F 2002/4475* (2013.01); *A61F 2002/448* (2013.01); *A61F 2002/4631* (2013.01); *A61F 2002/4635* (2013.01); *A61F 2002/4685* (2013.01); *A61F 2310/00017* (2013.01); *A61F 2310/00023* (2013.01); *A61F 2/46* (2013.01); *A61F 2002/4687* (2013.01)

(56) References Cited

U.S. PATENT DOCUMENTS

| | | |
|---|---|---|
| 6,224,607 B1 | 5/2001 | Michelson |
| 6,402,750 B1 | 6/2002 | Atkinson |
| 6,613,054 B2 | 9/2003 | Scribner |
| 6,641,582 B1 | 11/2003 | Hanson |
| 6,689,132 B2 | 2/2004 | Biscup |
| 7,083,623 B2 | 8/2006 | Michelson |
| 7,547,319 B2 | 6/2009 | Segal |
| 7,575,580 B2 | 8/2009 | Lim |
| 7,578,820 B2 | 8/2009 | Moore |
| 7,785,368 B2 | 8/2010 | Schaller |
| 7,803,188 B2 | 9/2010 | Justis |
| 7,828,807 B2 | 11/2010 | LeHuec |
| 7,887,538 B2 | 2/2011 | Bleich |
| 7,905,886 B1 | 3/2011 | Curran |
| 7,909,872 B2 | 3/2011 | Zipnick |
| 7,935,124 B2 | 5/2011 | Frey |
| 7,938,860 B2 | 5/2011 | Trieu |
| 7,993,378 B2 | 8/2011 | Foley et al. |
| 8,021,429 B2 | 9/2011 | Viker |
| 8,034,112 B2 | 10/2011 | Cauthen, III et al. |
| 2006/0265077 A1* | 11/2006 | Zwirkoski ................. 623/17.16 |
| 2007/0055275 A1* | 3/2007 | Schaller ..................... 606/92 |
| 2008/0125865 A1* | 5/2008 | Abdelgany ............... 623/17.16 |
| 2008/0221687 A1* | 9/2008 | Viker ........................ 623/17.16 |
| 2008/0234827 A1 | 9/2008 | Schaller |
| 2008/0312743 A1* | 12/2008 | Vila et al. ................. 623/17.16 |
| 2009/0005871 A1* | 1/2009 | White et al. .............. 623/17.11 |
| 2009/0012612 A1 | 1/2009 | White |
| 2009/0240334 A1 | 9/2009 | Richelsoph |
| 2009/0270873 A1 | 10/2009 | Fabian |
| 2010/0004750 A1 | 1/2010 | Segal |
| 2010/0023019 A1 | 1/2010 | Fuhrer et al. |
| 2010/0198263 A1 | 8/2010 | Siegal |
| 2011/0009969 A1 | 1/2011 | Puno |
| 2011/0071536 A1 | 3/2011 | Kleiner |
| 2011/0077740 A1 | 3/2011 | Perez-Cruet |
| 2011/0319995 A1 | 12/2011 | Voellmicke et al. |

FOREIGN PATENT DOCUMENTS

| | | |
|---|---|---|
| WO | WO2006091744 | 8/2006 |
| WO | WO2007022194 | 2/2007 |
| WO | WO2008103781 | 8/2008 |
| WO | WO2008103832 | 8/2008 |

* cited by examiner

SPINAL SURGERY IMPLANTS AND DELIVERY SYSTEM

FIELD AND BACKGROUND OF THE INVENTION

The invention relates generally to spinal surgical devices, and more particularly to spinal surgery implants and a corresponding delivery system. An intervertebral multi-link implant has been disclosed in co-assigned PCT patent application publication no. WO 2008/084479 and is incorporated by reference herein.

SUMMARY OF THE INVENTION

Embodiments of the present invention disclose a spinal surgery tool system including an elongated conduit and an implant. The implant assumes a straight configuration within the elongated conduit and is deployable from the elongated conduit into a closed or nearly-closed loop configuration for deployment interposed between two tissue surfaces to define an enclosed volume. The conduit and the implant are configured such that, when the implant is deployed in the loop configuration, an opening formed in a proximal portion of the implant forms a contiguous channel with a passageway along the conduit so as to provide a continuous access channel along the elongated conduit into the enclosed volume.

According to a further feature of an embodiment of the present invention, the spinal surgery tool system further includes an injector configured for insertion along the access channel for introducing biocompatible material, into the enclosed volume, selected from the group of biocompatible materials consisting of: bone particles, drugs, biological substances, bone substitutes, demineralized bones, bone matrices, and cement.

According to a further feature of an embodiment of the present invention, the spinal surgery tool system further includes an endoscope configured for insertion along the access channel for imaging a region within or adjacent to the enclosed volume.

According to a further feature of an embodiment of the present invention, the spinal surgery tool system further includes at least one surgical tool configured for insertion along the access channel for acting on a region within or adjacent to the enclosed volume.

According to a further feature of an embodiment of the present invention, the spinal surgery tool system further includes an irrigation arrangement for insertion along the access channel for flushing out fluids and tissues from the enclosed volume.

According to a further feature of an embodiment of the present invention, advancing and removing the implant is done using a carrier mechanism through the elongated conduit.

According to a further feature of an embodiment of the present invention, the carrier mechanism enables connecting a holder inserted to the elongated conduit, and wherein the holder includes a tensing element used for folding the implant to its closed loop configuration.

According to a further feature of an embodiment of the present invention, the carrier mechanism includes a manually operable actuator for controlling the deployment and the removal of the implant.

According to a further feature of an embodiment of the present invention, the implant is fully closed in its closed loop configuration.

According to a further feature of an embodiment of the present invention, the implant is partially closed in its closed loop configuration wherein a bridging element connects the distal and proximal ends of the implant.

According to a further feature of an embodiment of the present invention, the implant has a proximal link, middle links and a distal link wherein the proximal link interconnects with the distal link in its closed loop configuration.

According to a further feature of an embodiment of the present invention, a method for performing spinal surgery is disclosed. The method includes the steps of: (a) preloading an implant in a straight configuration to an elongated conduit, (b) folding the implant to a closed or nearly closed loop configuration in between two tissue surfaces, and (c) providing an access channel to the enclosed volume of the implant contiguous along the carrier mechanism and the elongated conduit.

According to a further feature of an embodiment of the present invention, the method for performing spinal surgery further includes the step of injecting a quantity of biocompatible materials into the implant's enclosed volume through the provided access channel selected from the group of biocompatible materials consisting of: bone particles, drugs, biological substances, bone substitutes, demineralized bones, bone matrices, and cement.

According to a further feature of an embodiment of the present invention, the implant is deployed in an intervertebral space and the two tissue surfaces are two vertebral endplates, and wherein the particulate solid comprises particles of bone injected in a plurality of injection steps, wherein less than 3 cubic centimeters of bone particles is injected at a time, and wherein the injected bone particles are compacted so as to fill the enclosed volume and ensure contact with the vertebral endplates above and below the loop configuration.

According to a further feature of an embodiment of the present invention, the method for performing spinal surgery further includes the step of removing part of an intervertebral disc using at least one surgical tool inserted into the enclosed volume through the elongated conduit and the access channel.

According to a further feature of an embodiment of the present invention, the method for performing spinal surgery further includes the step of preparing the vertebral end plates using at least one surgical tool inserted into the enclosed volume through the elongated conduit and the access channel.

According to a further feature of an embodiment of the present invention, the method for performing spinal surgery further includes the step of flushing out fluids and tissues from the in between two tissue surfaces through the provided access channel and the elongated conduit.

According to a further feature of an embodiment of the present invention, a method for performing spinal surgery is disclosed. The method includes the steps of: (a) providing a tool system comprising: (i) an elongated conduit having at least one opening, (ii) a first surgical device configured for advancing along the conduit in engagement with the conduit so as to follow a first predefined path of motion along the conduit and out through the at least one opening, and (iii) a second surgical device configured for advancing along the conduit in engagement with the conduit so as to follow a second predefined path of motion along the conduit and out through the at least one opening.(b) inserting the conduit so that the distal end is in a position with the at least one opening facing a target volume within the spinal column. (c) introducing the first surgical device along the conduit so that the first surgical device follows the first predefined path of motion within the target volume, and (d) introducing the second surgical device along the conduit so that the second surgical device follows the second predefined path of motion within the target volume.

According to a further feature of an embodiment of the present invention, the elongated conduit at least one opening is a lateral opening.

According to a further feature of an embodiment of the present invention, the elongated conduit has multiple openings, and wherein the steps of introducing the first and second surgical devices along the conduit and out of the conduit are performed through two different openings selected from the conduit's multiple openings.

According to a further feature of an embodiment of the present invention, the method for performing spinal surgery further includes the step of fixating the conduit's position relative to the spinal column.

According to a further feature of an embodiment of the present invention, the elongated conduit has a distal end with at least one lateral or frontal opening, and wherein the elongated conduit defines a plurality of inflection points for introducing at least the first surgical device and the second surgical device into the body along different corresponding predefined paths of motion.

According to a further feature of an embodiment of the present invention, an implant, includes an elongated element having a plurality of flexing regions, wherein the implant assumes a straightened configuration for introduction into the body, and is deployable into a closed or nearly-closed loop configuration for deployment interposed between two tissue surfaces to define an enclosed volume, the implant being configured such that, when the implant is deployed in the loop configuration, an opening is formed in a proximal portion of the implant to allow access to the enclosed volume.

According to a further feature of an embodiment of the present invention, the elongated element is formed from a plurality a segments interconnected at the flexing regions, and wherein the opening is implemented as a passageway passing through a proximal one of the segments.

According to a further feature of an embodiment of the present invention, an implant, includes an elongated element having a plurality of flexing regions, wherein the implant assumes a straightened configuration for introduction into the body, and is deployable into a closed or nearly-closed loop configuration for deployment interposed between two tissue surfaces to define an enclosed volume, the implant being configured such that, when the implant is deployed in the loop configuration, an opening is formed in a distal portion of the implant to allow access to the enclosed volume.

According to a further feature of an embodiment of the present invention, the elongated element is formed from a plurality a segments interconnected at the flexing regions, and wherein the opening is implemented as a passageway passing through a distal one of the segments.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings.

DESCRIPTION OF THE PREFERRED EMBODIMENTS

Embodiments of the present invention provide a spinal surgery tool system and a method for deploying implants through elongated conduit that is used as a working channel that allows access to the implant's enclosed volume. A further aspect of the present invention relates to the use of a single conduit to determine predefined paths of motion for each of a plurality of surgical devices, which may be implants or tools. The various aspects of the invention will be illustrated herein primarily by reference to a non-limiting example of a system and method for performing vertebral fusion, but it will be appreciated that the various aspects of the present invention are equally applicable to a wide range of other spinal and other surgical procedures.

Hereinafter, the term surgical device includes surgery tools and implants and the term target volume refers to a volume on which the surgical procedure is to be executed, such as, the volume of an (evacuated) intervertebral disc.

The intervertebral body fusion system includes an implant and a delivery system, the latter typically including an elongated conduit, a holder and a carrier mechanism. According to certain embodiments of the present invention, an implant assumes a straight configuration within the elongated conduit and is deployable from the elongated conduit into a closed or nearly-closed loop configuration for deployment interposed between two tissue surfaces to define an enclosed volume. In the context of the present description and claims, the phrase "nearly closed" refers to any configuration in which any remaining gap between the distal and proximal ends of the implant is smaller than a lateral dimension of the implant when straightened, giving an overall visual and functional effect similar to a closed loop. Except where explicitly stated to the contrary, the various aspects of the present invention may also be implemented to advantage with a C-shaped implant, i.e., having a relatively large open part. The elongated conduit and the implant are preferably configured such that, when the implant is deployed in the loop configuration, an opening formed in a proximal portion of the implant forms a contiguous channel with a passageway along the conduit so as to provide a continuous access channel along the elongated conduit into the enclosed volume. The access channel to the enclosed volume of the implant allows a variety of clinical procedures to be performed through the conduit working channel such as bone injection, and insertion of part of an imaging system, such as the tip of an endoscope.

According to embodiments of the present invention, the implant enclosed volume is connected with the elongated conduit's lumen through the proximal part of the implant. However, the access to the enclosed volume may be done through other part of the implant, for example the distal part, and is not limited to the proximal part as described in some embodiments of the present invention.

During deployment of the implant, the implant is preferably supported by an elongated holder which is interconnected with the implant, and which serves to advance and deploy the implant. Accordingly, in certain preferred implementations of the present invention, access to the enclosed volume of the deployed implant is achieved through an internal channel formed along the length of the holder. This internal channel may be a fully closed lumen, or may be open on one or more side along the length of the holder.

Although the preferred implementation illustrated herein employs an enclosed conduit, it should be noted that this is one example of a range of different guide elements which may be used to guide the implant and other tools of the present invention to the desired location and preferably also to define a point of inflection at which deflection of the implant to its curved configuration occurs. By defining a point of inflection for the implant and/or various tools, the path followed by the tools within the body becomes well defined and repeatable as a function of the guide position. Alternate implementations of the invention employ other guide elements, such as an open external guide or a guide element extending along an inner recess of the implant up to the point of inflection.

According to a further aspect of the present invention, certain embodiments provide a method for performing spinal surgery. The method comprising the steps of (a) providing a tool system comprising an elongated conduit having a distal end with at least one frontal or lateral opening, a first surgical device configured for advancing along the conduit in engagement with the conduit so as to follow a first predefined path of motion along the conduit and out through the at least one frontal or lateral opening, and a second surgical device configured for advancing along the conduit in engagement with the conduit so as to follow a second predefined path of motion along the conduit and out through the at least one frontal or lateral opening. (b) inserting the conduit so that the distal end is in a position with the at least one frontal or lateral opening facing a target volume within the spinal column; (c) introducing the first surgical device along the conduit so that the first surgical device follows the first predefined path of motion within the target volume; and (d) introducing the second surgical device along the conduit so that the second surgical device follows the second predefined path of motion within the target volume.

The predefined path of motion described above is a path followed by each point and not necessarily a sequential motion along a common path.

Once the conduit is deployed, the surgeon may decide on doing a wide range of surgical procedures through the working channel of the conduit, including but not limited to and combination of: (a) inserting surgical tools to perform discectomy or otherwise evacuate tissues or fluids from the working volume; (b) inserting surgical tools to prepare adjacent tissue for a subsequent procedure, e.g., vertebral body endplate preparation in the case of vertebral fusion; (c) introducing a trial implant and/or a final implant into the working volume; (d) injecting a filling material into the working volume, or into an enclosed volume defined by the implant, e.g., introduction of bone particles to the implant's enclosed volume for fusion; and (e) insertion of part of an imaging system or other diagnostic tools into the working volume and/or into an enclosed volume defined by the implant at any stage of the procedure to facilitate or verify correct performance of one or more stages of a procedure or any other useful action.

Figure 1:
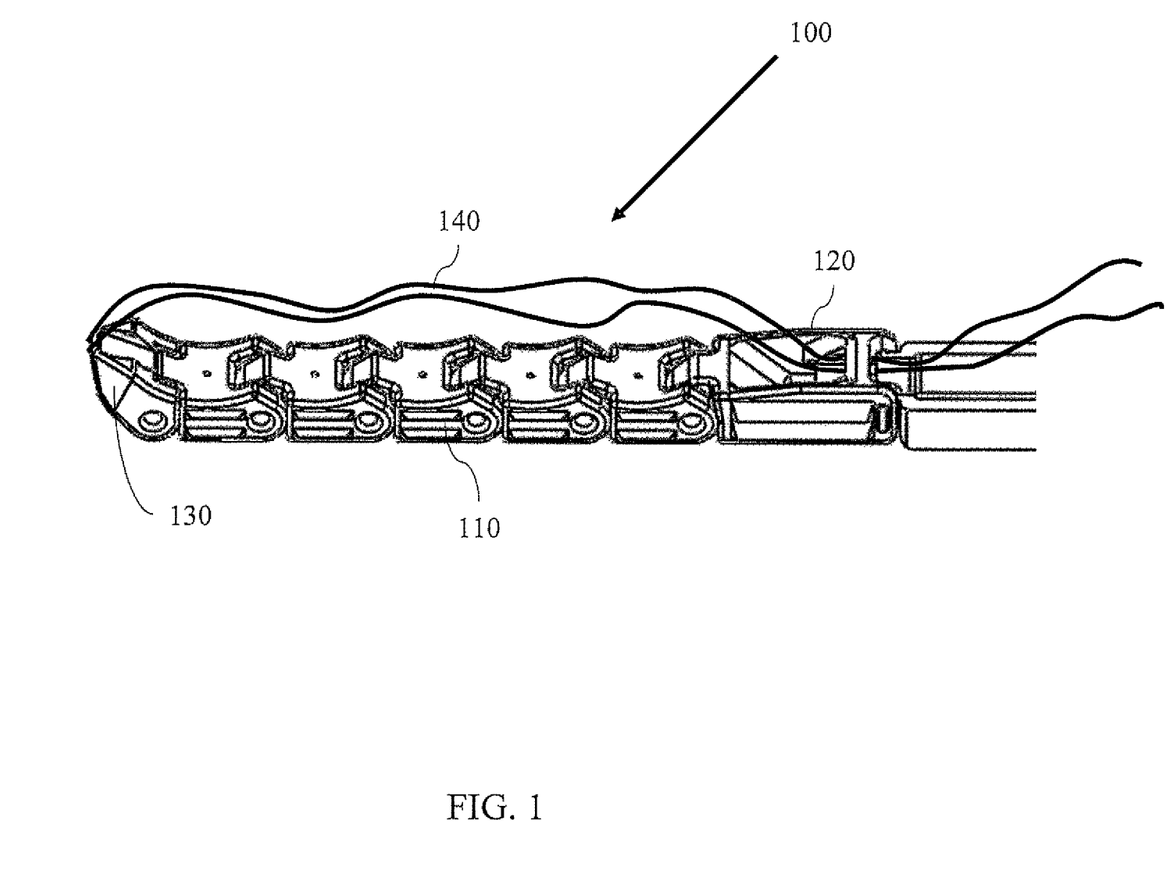
FIG. 1 illustrates an implant and a tensing element, according to an embodiment of the present invention.

FIG. 1 illustrates an implant and a double-strand string tensing element, according to embodiments of the present invention. Multi-link circular implant 100 is shown in its straight configuration. Multi-link implant 100 has a number of mid links 110, a distal link 130, and a proximal link 120 which are typically manufactured from either plastic (e.g. Poly Ether Ether Ketone, Ultra High Molecular Weight Polyethylene, etc.) or metal (e.g. Titanium, stainless steel, etc.), or a combination of metal and plastic. The implant's links are connected using effective hinges, and may be made for example of external axes of a radio-opaque metal such as Tantalum, of integral joints, or of any other kind of hinges, open or closed. As shown later, these axes facilitate deployment of the device inside an evacuated intervertebral disc volume and to reach a closed loop configuration forming an enclosed volume inside the implant. Optionally, the multi-link implant may be integrally formed from a single material with integral joints between "links" or "segments" of the structure. The term "multi-link" or "multi-segment" is also used to refer to such integrated structures, since they still provide the function of relatively rigid "links" or "segments" which are interconnected at effective hinges.

A tensing element 140 may be a one strand string or a multiple strand string and a double-strand string is shown in FIG. 1. The double-strand string 140 is used to fold implant 100 to its closed loop configuration as it emerges from a conduit 150 shown in FIG. 3. In the example shown here, double-strand string tensing element 140 is placed externally to mid links of device 100. It is placed at a distance from the axes of device 100 therefore significant moments can be applied in between links of implant 100, thus ensuring that the multi-link implant 100 drives properly through any leftover tissues and flexes fully. Tensing element 140 preferably guides the distal link to the proximal link when the multi-link implant is in closed loop configuration as shown in FIGS. 3a-3f herein below.

The tensing element 140 may optionally be manufactured of either plastic (e.g. UHMWPE, PEEK, etc.), or metal (e.g. stainless steel, Nitinol, etc.), either in a braided/multi filament configuration or a single filament one, having either a circular cross section or a strip like one (e.g. a rectangular cross section). The tensile element can also be made of either a non-biodegradable material or a bio-degradable one (such as, Polyglycolic Acid, Polylactic Acid, etc.).

Optionally, tensing element 140 may be designed as a spring. In other embodiments the tensing element may be substantially elastic (e.g. having a spring-like design or made of a shape memory alloy such as Nitinol) and firmly connected to the proximal link of the implantable device.

According to another set of preferred options, the implant may be formed with internal or external biasing elements (springs) deployed between adjacent segments to bias the segments towards their deflected states, or the implant may be formed with integral hinges which are inherently biased (e.g., by use of shape memory materials or regular elastic properties) to the deflected state.

According to embodiments of the present invention, a delivery system for implanting an intervertebral implant includes an elongated conduit, a holder, an implant and a carrier mechanism for deploying the implant using the elongated conduit.

Figure 6:
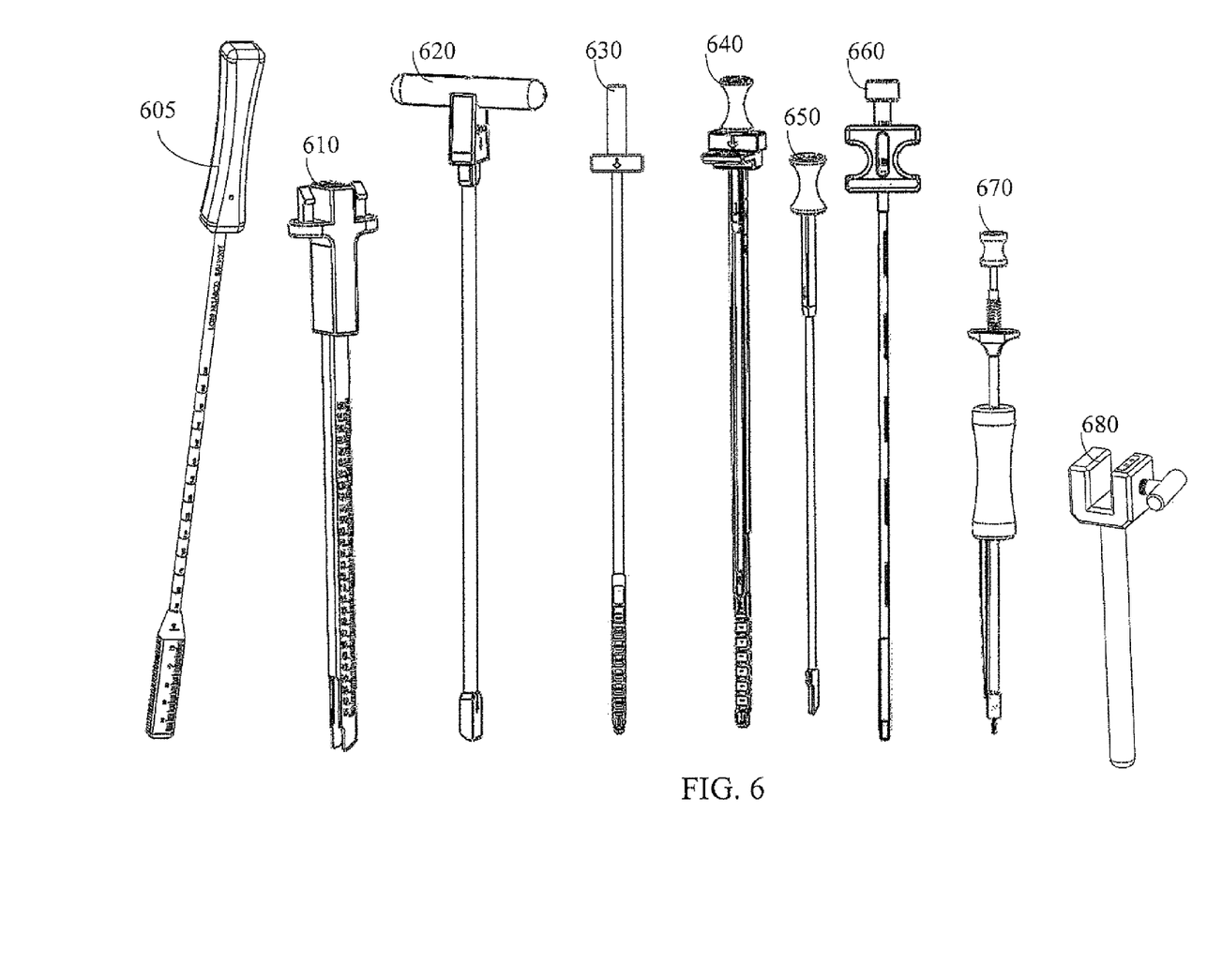
FIG. 6 illustrates the spinal surgery tool system, according to an embodiment of the present invention.

The preparation steps for the implantation of an intervertebral implant preferably include a posterior mid-line or other suitable surgical incision. A bullet-tip preparation tool (FIG. 6, 605) is preferably used to prepare an opening for insertion of the conduit. Depending upon the approach, and particularly for a TLIF or PLIF approach, a facet cutter or cartilage cutter may be used to provide the required access path to the intervertebral (or intravertebral) space. The preparation tool preferably has teeth on its top and bottom edges to shave off cartilage during inertion and removal. An elongated conduit (FIG. 6, 610) is preferably then introduced, serving as a guide for all the subsequent tools and operations. The proper positioning of the conduit distal end may be validated with radiographic imaging. The conduit is preferably fixated, either to an external rail, or to a pedicle screw, for example using clamp 680 (FIG. 6). In some cases, a practitioner may prefer to operate the system by hand without rigid fixation. In certain preferred implementations, the conduit may be an expanding conduit which serves to perform distraction of the intervertebral space as it expands, thereby also accommodating a range of sizes of implants using the same conduit. Examples of suitable expanding conduits are described in co-pending PCT Patent Application No. PCT/IB 11/050622 and U.S. Provisional Patent Application No. 61/506,102, both of which are hereby incorporated by reference as if set out entirely herein.

Preparation for implantation continues with partial or complete discectomy, in which the disc and the vertebral endplates' osteophytes are removed with a scraper and a distractor, forming an evacuated disc volume. According to certain particularly preferred embodiments of the present invention, the discectomy and the endplates cleaning preparation steps described above may be performed via the elongated conduit that acts as a working channel. Particularly preferred but non limiting examples of suitable discectomy tools that may be used via the conduit of the present invention include mechanical discectomy devices described in U.S. patent application Ser. No. 13/020,103 and electrical discectomy device described in U.S. Provisional Patent Application No. 61/485, 140, both of which are hereby incorporated by reference as if set out entirely herein. It will be noted that the use of conduit-based discectomy tools provides accurate alignment between the discectomy procedure and the subsequent deployment of the implant, thereby ensuring precise removal of the correct volume of tissue. In certain cases, where sufficient precision can be achieved, this may allow omission of the "trial implant" step described below for testing the size and fit of the implant within the evacuated volume.

Figure 5:
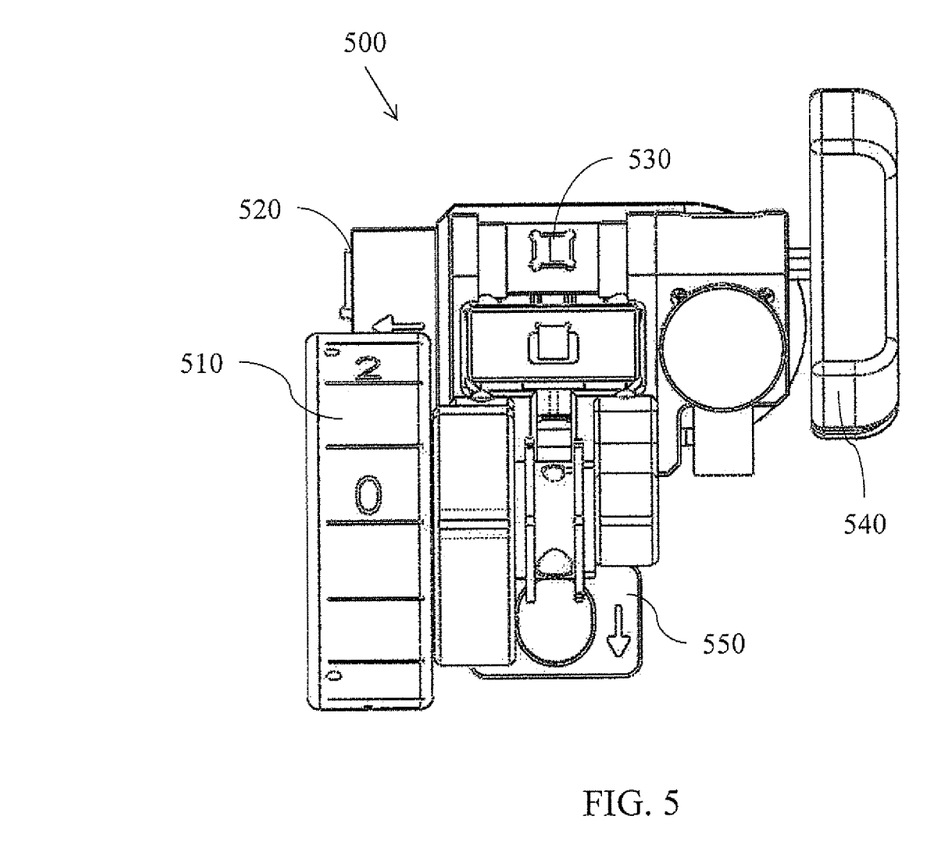
FIG. 5 illustrates a top view of the carrier mechanism, according to an embodiment of the present invention.

According to certain embodiments of the present invention, an implant may be deployed using a holder (shown in FIGS. 2a-2b and FIG. 6, 640) through the elongated conduit (shown in FIG. 6, 610) using a carrier mechanism (shown in FIG. 5, 500). Furthermore, the elongated conduit allows a variety of invasive clinical procedures to be performed safely, where the conduit acts as a working channel isolated from the patient's body allowing access to the enclosed volume of the implant inside the evacuated disc volume. The elongated conduit (shown in FIG. 6, 610) is supplied with different heights, typically 7, 8, 10, 12 and 14 mm, corresponding to implants with different heights. The surgeon may up-size or down-size the conduit height used according to the size of implant to be deployed.

Figure 2A:
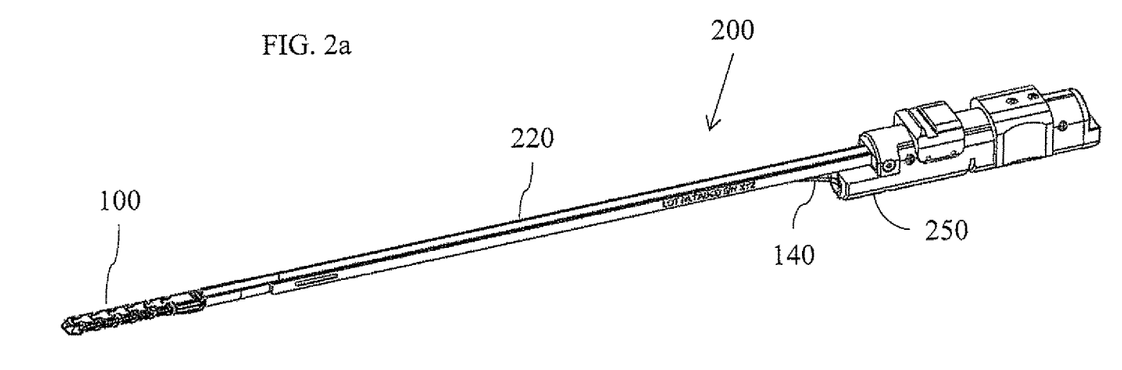
FIGS. 2a and 2b are upper and lower isometric view, respectively, of an implant and implant holder according to an embodiment of the present invention.
Figure 2B:
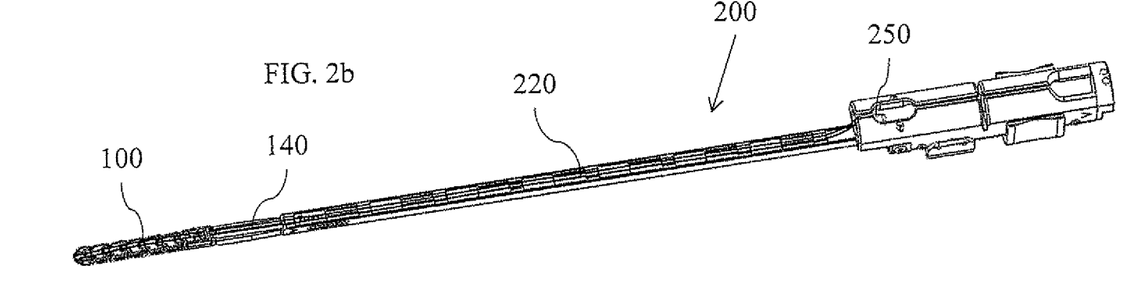

FIGS. 2a and 2b illustrate implant 100 connected to holder 200, according to embodiments of the present invention. Holder 200 is inserted into an elongated conduit having a distal end with a lateral opening (shown in FIG. 6, 610) and is used to advance and deploy intervertebral implant 100 which is interconnected to the distal end of the holder 200. Holder 200 itself is preferably formed with a hollow elongated body 220 which provides an internal channel that allows insertion of a filling device (e.g., a bone injector) to allow filling of an enclosed volume within the deployed implant while the implant is still connected to the holder. It should be noted that the internal channel need not be completely enclosed, as exemplified by the openings in the lower surface of the channel in the example shown in FIG. 2b.

In the non-limiting implementation shown here, holder 200 includes a retention arrangement which locks onto a proximal segment of implant 100 during insertion and deployment, and a release mechanism which releases the retention arrangement after deployment and filling of the implant. It should be noted however that alternative implementations are possible. In one alternative set of embodiments, a disposable holder 200 is initially integrally formed (or semi-permanently attached) to the implant via a breakable linkage, which is broken at the end of the deployment and filling process.

Double-strand string tensing element 140 is connected to the implant distal link, through a slit in the proximal link, and has an anchor at its other end 250 for connecting the double-strand string to the carrier mechanism (shown in FIG. 5). Holder 200 is clicked-in into the carrier mechanism through its base 230. Holder 200 has a releaser button used to release the multi-link implant from the holder. The double-strand external string 140 used to deflect the implant to its closed loop configuration is only one example of a tensing element and other suitable mechanism for deflecting the implant to its closed loop configuration may be used, including one-strand or multiple strands strings, an internal tensing element, a built-in spring or inherent resilient biasing of the implant.

Figure 3A:
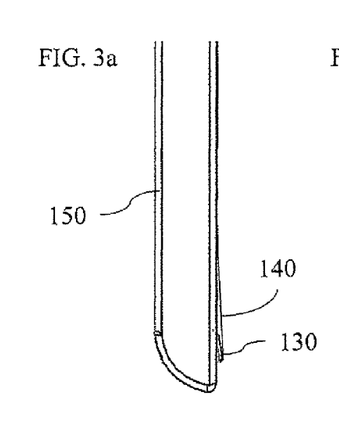
FIGS. 3a-3f illustrate successive stages of deployment of a multi-link implant as it emerges from a conduit and deflects to its closed loop configuration, according to an embodiment of the present invention.
Figure 3B:
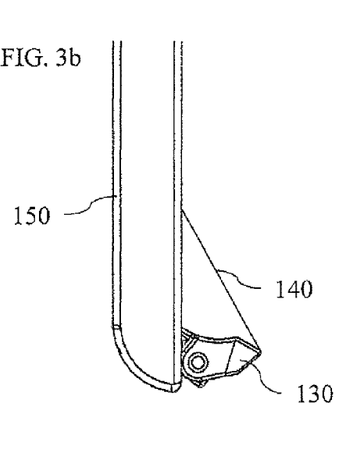
Figure 3C:
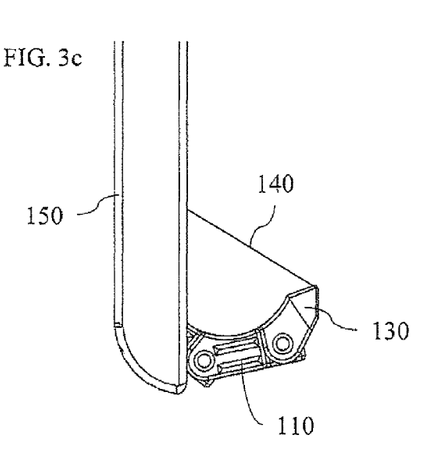
Figures 3D, 3E, 3F:
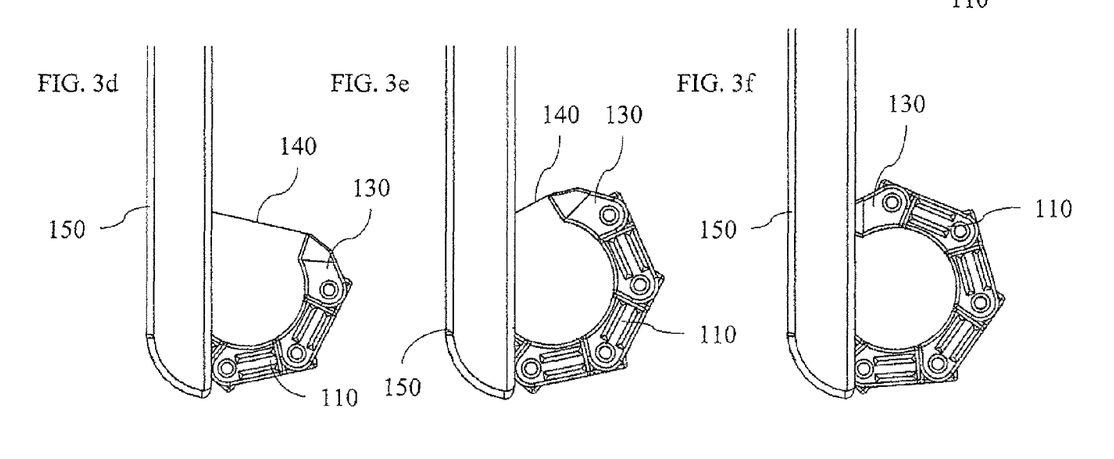

FIGS. 3a-3f illustrate the multi-link implant as it emerges out and deflects to its closed loop configuration, according to certain embodiments of the present invention. The multi-link implant is loaded into the elongated conduit in a straight configuration as shown in FIG. 2a, 100. As the multi-link implant emerges out of the elongated conduit distal end lateral opening, each link deflects due to the force applied by the double-strand string tensing element 315. FIGS. 3a-3f show how the multi-link implant deflects progressively following a predefined path of motion along the conduit and out through the conduit lateral opening. Only the distal link 130 is shown at FIG. 3a while the multi-link implant reaches its closed loop configuration gradually as shown in FIGS. 3a-3f. The implant distal link is guided by the double-strand string 315 to the implant proximal link located inside the elongated conduit (not visible in FIGS. 3a-3f) and is still attached to the holder (FIG. 2, 200).

According to embodiments of the present invention, the inflection point at which the implant emerges out and folds out of the elongated conduit does not have to be at the conduit tip end as shown in FIG. 3a, and instead could be at a distance from the tip end. Accordingly, the tip end may be used for delivering medication to a location outside the implant for example. The elongated conduit may optionally have features (such as internal tracks at different widths) to define multiple inflection points at which different devices are deflected to deploy laterally at different positions along the length of the conduit, or to emerge from the same opening at different angles. Thus, the elongated conduit may have two or more openings used for deploying at least a first surgical device and a second surgical device into the body along different predefined paths of motion of each surgical device. Furthermore, the elongated conduit may have multiple frontal or lateral openings allowing for the deployment of more than one surgical device sequentially or simultaneously and wherein the multiple openings may be frontal or lateral openings. As a result, it is possible to define different predefined paths of motion to be followed by different tools, for example, for performing surgical procedures in different sub-regions of the volume to be treated. By way of one non-limiting example, this may be implemented using a relatively narrower and relatively wider tool or implant, and with a first narrow opening and a second wider opening in the conduit. The narrower tool fits through the narrower opening and is therefore deployed via an inflection point at a relatively proximal position along the conduit, whereas the wider tool is maintained in its straightened state as it passes the narrower opening and only undergoes inflection to be deployed laterally when it encounters the wider opening at a more distal position along the conduit. In other cases, the point of inflection for a tool or implant which is "undersized" relative to the conduit can be adjusted by use of a dedicated insert, sleeve or conduit-liner inserted between the tool and the conduit so as to block deflection of the tool or implant until it reaches a desired location along a relatively elongated lateral opening in the conduit.

According to embodiments of the present invention, the elongated conduit may be aimed anteriorily towards the center of the evacuated disc volume. However, any lateral insertion direction may be implemented by clinicians and the proper positioning of the conduit distal end inside the evacuated disc volume may be validated with radiographic imaging.

Figure 4A:
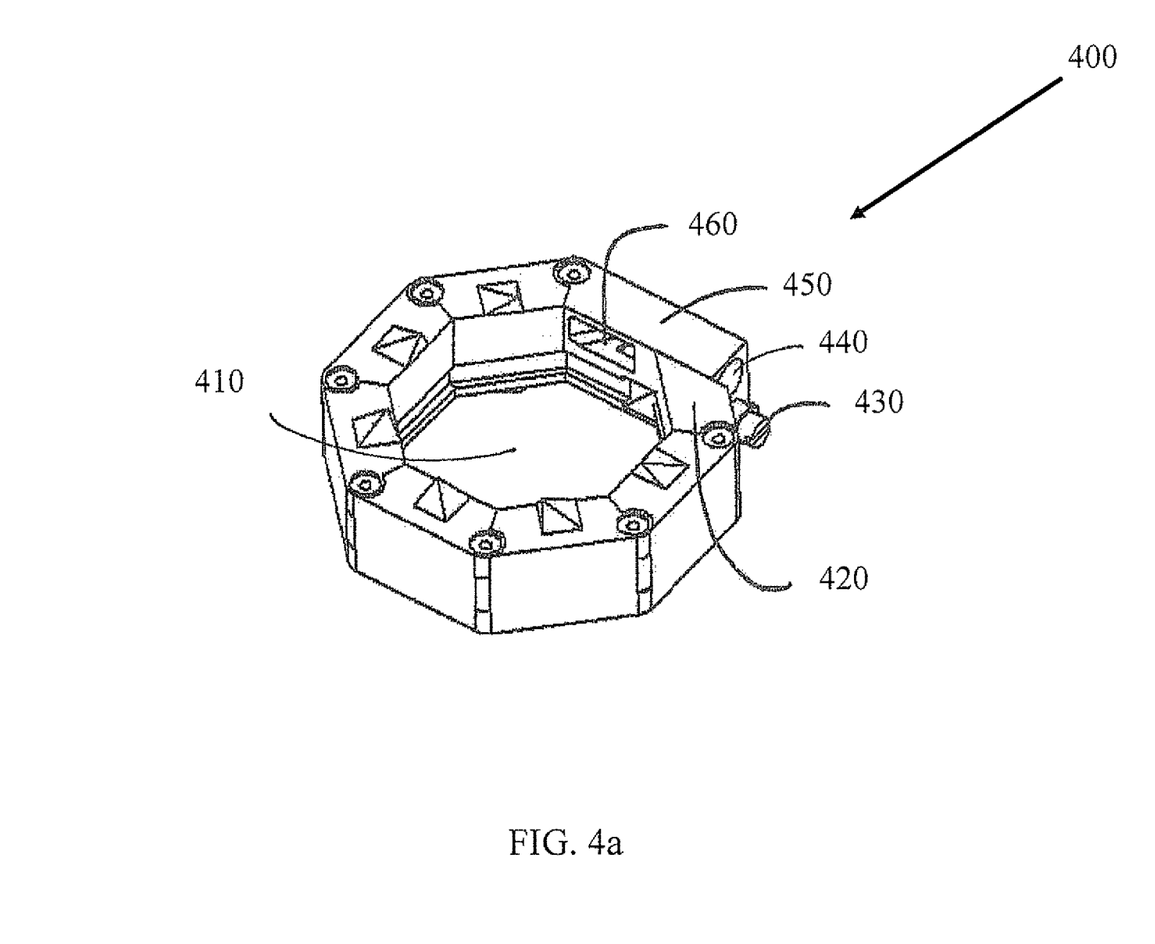
FIG. 4a illustrates an exploded view of an implant in its closed loop configuration, according to an embodiment of the present invention.

FIG. 4a illustrates exploded view of the implant in its closed loop configuration, according to embodiments of the present invention. When the multi-link implant 400 is closed, it forms an enclosed volume 410, which is connected through slit 460 and channel 440 to the conduit 610 (shown in FIG. 6). The distal link 420 is embedded within the proximal link 450 and a screw 430, which is pre-assembled inside proximal link 450, may be driven into a bore of the distal link 420 in order to lock implant 400 in its closed loop configuration. Alternative locking mechanisms may replace screw 430, such as a bayonet mechanism or flexible latches and snaps which may be embedded within either the proximal link 450 or the distal link 420. According to embodiments of the present invention, tensing element 140 may be used to tie the distal to the proximal links, used as an alternative locking mechanism instead of screw 430.

Slit 460 and channel 440 create the access channel that connects the enclosed volume of the folded implant to the elongated conduit lumen and further to the carrier mechanism (shown in FIG. 5). The surgeon may insert part of an imaging system, such as the end of an endoscope, through the carrier mechanism and further through the elongated conduit lumen to the implant's access channel. Furthermore, the surgeon may insert surgical devices for preparing the vertebral end plates through the working channel to the implant's access channel and to the implant's enclosed volume. Furthermore, fluids and tissues may be flushed out through the implant's access channel and through the carrier mechanism and further through the elongated conduit. Furthermore, the surgeon may open, reposition and remove the multi-link implant using a remover plunger (shown in FIG. 6, 670) through the carrier mechanism and further through the elongated conduit during the implantation or later in another clinical procedure.

Figures 4B, 4C, 4D:
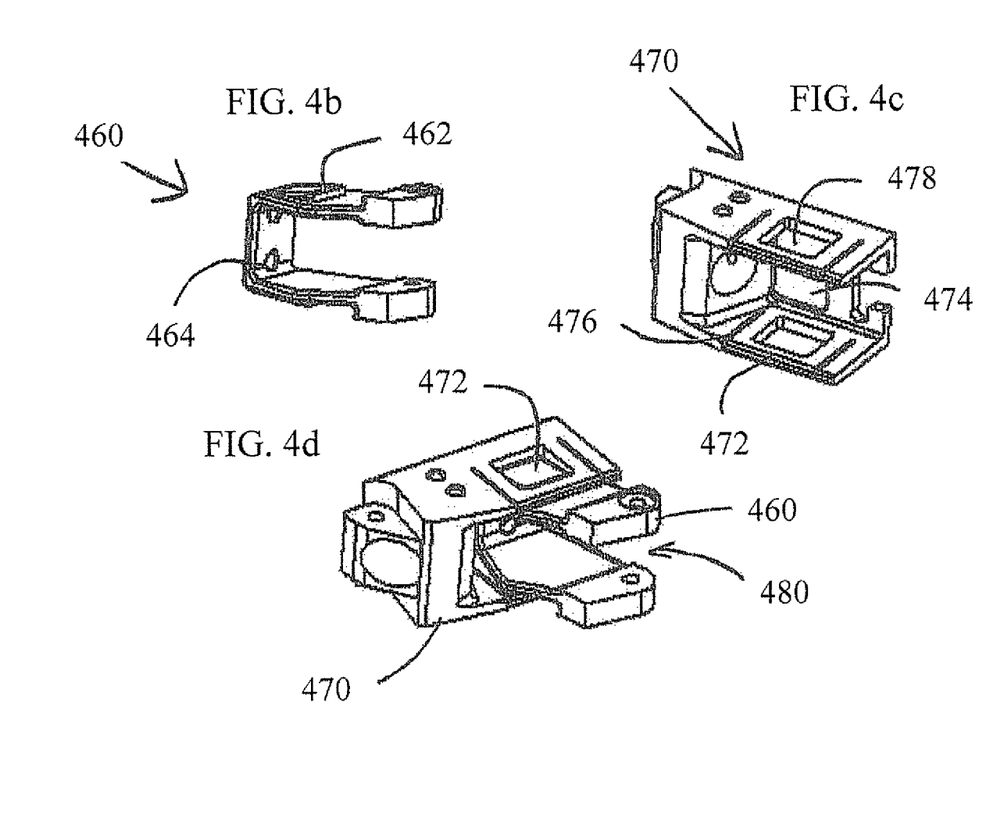
FIGS. 4b-4d illustrate an optional distal link 560, a proximal link 570 and their final assembly once the implant is in its closed loop configuration.

FIGS. 4b-d illustrate the optional distal link 460, the proximal link 470 and their final assembly once the implant is in its closed loop configuration. Due to the slits 476, proximal link 470 has flexible latches 472, which lock the device at its final closed configuration by grasping prominences 462 of distal link 460. Along its movement inside the target volume the distal link 460 may carry along a clinging disc or a bone tissue. Slits 478 and 474 ensure that these tissues do not interfere with the locking of the multi-link implant. Through these slits that create the access channel to the enclosed volume of the implant, these tissues may be moved out of the implant. Optionally, the pulling element double-strand string (shown in FIG. 1 140) is wired through holes 464 and through slit 474. The elements 460 and 470 are distal and proximal links of the multi-link implant that enable the snap-like locking mechanism.

Another locking mechanism may be "bayonet"-like (not shown). Due to their unique construction, the proximal 470 and distal links 460 are locked and integrated in a way which forms a large slit 480 for connecting a large delivery conduit. The slits 480, 478 and 474 create the access channel that enables injection of bone particles into the implant enclosed volume at its closed configuration. In alternative implementations, fastening of the distal and proximal segments may be achieved simply by tying a tensioning element (string) that passes through apertures in both distal and proximal segments. According to a still further implementation, the distal and proximal segments may not be directly fastened to each other, and may even not be completely closed against each other.

Figures 4E, 4F, 4G:
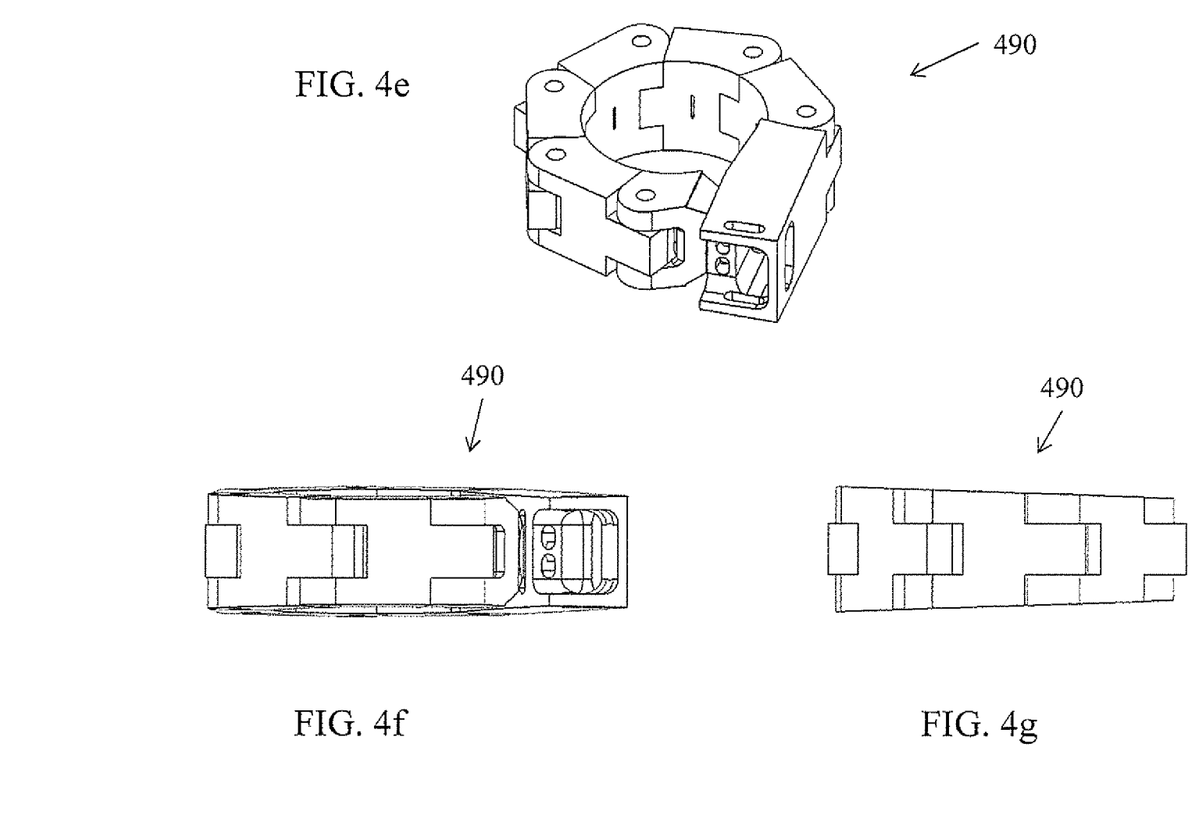
FIGS. 4e-4g show isometric, rear and side views, respectively, of a further closed loop implant, constructed and operative according to an embodiment of the present invention.

FIGS. 4e-4g show a variant of the implant of FIG. 4a, generally designated 490, constructed and operative according to an embodiment of the present invention. Implant 490 is formed with graduated width such that, when deployed, it provides lordotic angle correction, being thicker towards the anterior side of the loop and thinner at the posterior side. In all other respects, the structure and operation of implant 490 will be understood by analogy to the other embodiments described herein.

FIG. 5 illustrates the top view of a carrier mechanism, according to embodiments of the present invention. The carrier mechanism preferably controls the insertion and/or removal of a plurality of tools and devices during the procedure, including the multi-link implants, the bone injector and the removal plunger. In the particular non-limiting implementation illustrated here, the carrier mechanism includes a string wheel 510 for applying and releasing tension in a string causing deflection of the implant, a carrier button 520 for controlling locking and/or releasing of engagement between the carrier mechanism and the conduit, an access window 530 through which devices are inserted into the conduit, a deployment knob 540 for controlling advancing and withdrawing of the implant and/or tools, and a removal button 550 for controlling locking and/or releasing of engagement between the implant holder (or other tools) and the carrier.

It should be noted that many variant implementations of the carrier mechanism are possible. For example, instead of a deployment knob for advancing and retracting the implant holder, a pistol-grip or squeeze-handle actuator may be used to advance a linear ratchet structure. In other cases, a rotating actuator with an axis of rotation aligned with the length of the conduit may be used. Similarly, alternative mechanisms may be provided for applying, releasing and controlling tension in the string, or the tensioning element may be completely omitted in favor of an alternative biasing mechanism for biasing the implant to its loop configuration. These and other variants and all within the capabilities of a person having ordinary skill in the art.

After the preparation steps described herein above are completed and the proper positioning of the conduit inside the evacuated intervertebral disc volume is confirmed by radiography or other suitable techniques, a trial implant located at the distal end of the holder (shown in FIG. 6, 630) is preferably inserted. The trial implant's usage is to validate that adequate discectomy and distraction were performed, and that the intervertebral disc volume was evacuated fully, and that the evacuated disc volume is ready for an implantation of a permanent intervertebral body fusion multi-link implant.

After the first surgical device, the trial implant, is removed and the adequate discectomy and distraction of the evacuated intervertebral disc volume are validated, a second surgical device, namely, a permanent intervertebral implant may be deployed. The second surgical device follows a predefined path of motion along the conduit and out through the conduit at least one frontal or lateral opening, preferably following the same path followed by the trial implant. The multi-link permanent implant is loaded to the holder with a double-strand string 140 connected to its distal link 130 and passing through the slit in the proximal link 120 as shown in FIG. 1. After deploying the implant, a radiographic imaging is used to validate that the distal link 130 is embedded in place inside the proximal link 120. A closure pin shown in FIG. 6 650 may be inserted instead of a safety pin to the carrier mechanism and may be used to lock the distal link screw shown in FIG. 4a 430.

Bone injection may be performed using the bone injector tamp shown in FIG. 6 660. The surgeon may insert the bone injector tamp using the carrier mechanism through the conduit to the implant's access channel created by slits 440 and 460 shown in FIG. 4a and slits 472, 474 and 478 shown in FIG. 4c and FIG. 4d. The bone injector is used to inject bone particles into the implant enclosed volume. The bone particles are typically injected in 3 to 10 injection cycles, wherein typically less than 3 cubic centimeters of bone particles is injected at a time. The injected bone particles fill the multi-link implant and the evacuated disc volume fully, and are preferably stuffed under pressure so as to ensure intimate contact of the particles with the prepared bone surfaces, thereby greatly increasing the likelihood of successful fusion of the vertebrae. According to embodiments of the present invention, bone injector tamp 760 may be used to inject quantity of any particulate solid or other biocompatible material into the implant's enclosed volume through the provided access channel. The injected biocompatible materials may be drugs, biological substances, bone substitutes, demineralized bones, bone matrices, cement, etc.

A removal plunger 670 shown in FIG. 6, may be used to re-position or remove the multi-link implant after detachment from the conduit and the carrier mechanism. The remover plunger 670 grasps the implant proximal link. The plunger may be used to push the distal link from the proximal link and to open the multi-link implant. As the opened multi-link implant is pulled out by the remover from the evacuated disc volume it straightens inside the elongated conduit to its substantially straightened configuration.

FIG. 6 illustrates the spinal surgery tool system, according to embodiments of the present invention. The spinal surgery tool system includes an elongated conduit 610, the working channel through which all instruments and implants are introduced into the evacuated disc volume. A Plunger 620 may be used as a mandrel for the conduit insertion into the evacuated disc volume. A trial implant 630 may be used to confirm proper evacuation of the disc volume prior to implantation. A holder 640 is the interface between the implant and the carrier mechanism composed of a holder (attached to the implant), a releaser (releases the implant from the holder) and a safety pin (prevents premature release of the implant from the holder). A closure pin 650 may be used to lock and to ensure full closure of the implant in its closed loop configuration. A bone injector 660 includes tubes and tamps for injecting bone particles to the enclosed volume of the implant. A remover 670 may be used to remove an implant after it was detached from the holder. A fixator 680 may be used to attach the conduit to the surgical table.

Figure 7:
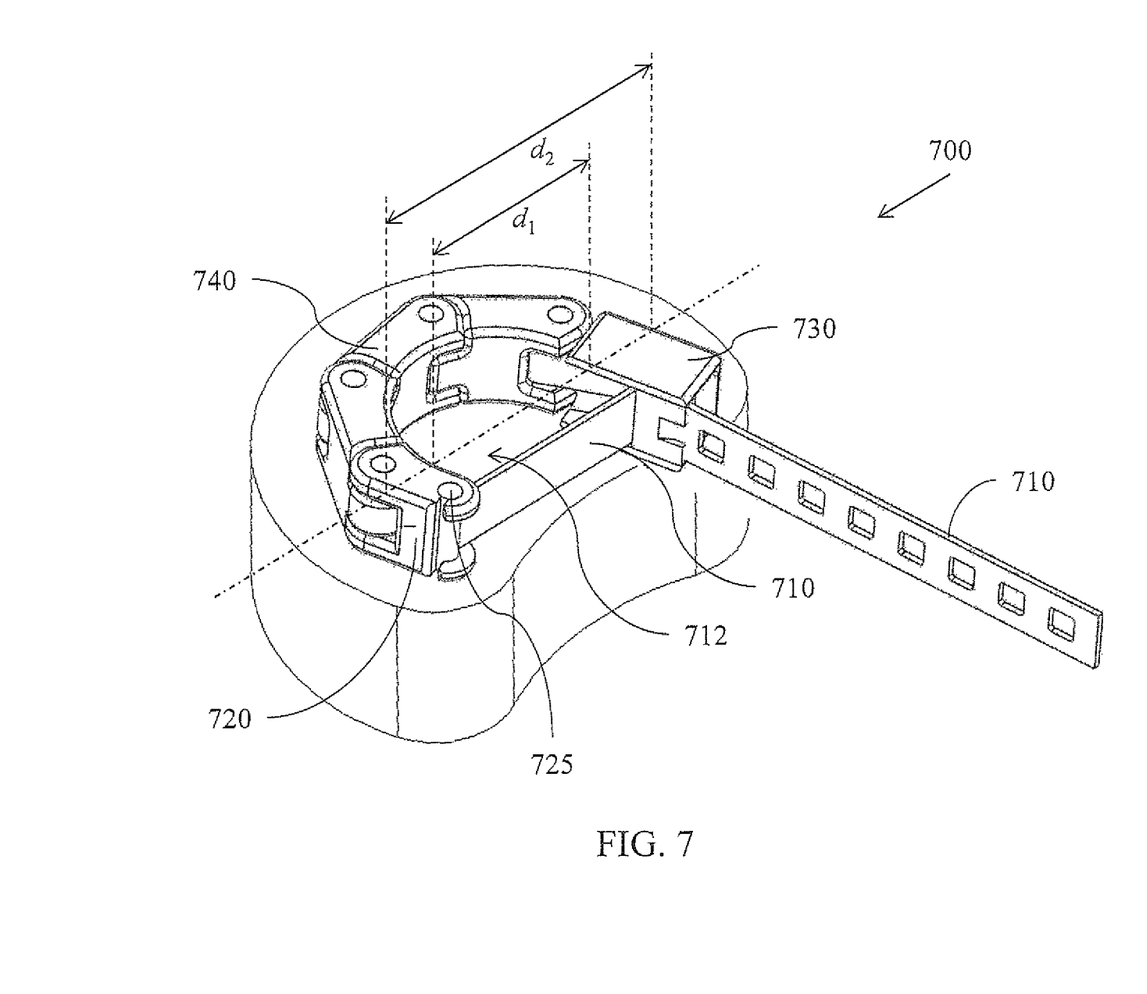
FIG. 7 illustrates another embodiment of an implant, according to an embodiment of the present invention.

FIG. 7 illustrates another embodiment of an implant, according to embodiment of the present invention. The implant 800 has a bridging element, here implemented as a flexible strip or ribbon 710 made, for example, of titanium or any other material with suitable mechanical and biocompatible properties, and of any desired width. A part of the titanium strip 715 in this case provides part of the closure of the loop of the implant, bridging between distal 720 and proximal 730 links. Attachment of the strip to the distal link is preferably at a hinged pin 725. A tail portion of strip 710 passes through the proximal link and is pulled tight during deployment of the implant into its loop configuration. A locking pin (not visible here) or other similar structure may engage openings in the strip so as to lock the strip in position relative to the proximal link after deployment. The titanium strip is optionally welded or otherwise fixed in position after insertion, strengthening the connection between the proximal 730 and distal 720 links. The multi-link implant 700 illustrated here has three medial links 740. However, other number of medial links may be used in embodiments of the present invention.

As seen in FIG. 7, the deployed closed loop structure of implants 700 has a central unobstructed void 712 which extends along a length $d_1$ corresponding to a majority of a maximum external dimension $d_2$ of the closed loop in the plane of the closed loop.

Alternative implementations of bridging elements according to this aspect of the present invention include one or more strings or other tension elements deployed to maintain the deflected state of the implant and preferably to also complete a geometrically closed shape that is at least partially enclosed by the bridging elements.

In addition to the multi-link hinged implants illustrated herein, the intervertebral implants of the present invention may be composed of other elongated elements having plurality of flexing regions, for example, provided by integral hinges or flexion regions. Other implants that may be deployed with the delivery system described hereinabove are in the scope of the present invention.

Furthermore, the present invention implants and delivery system may be used for any inter-body application other than intervertebral fusion, including but not limited to procedures in which the implant is introduced into an enclosed volume of a vertebral body. Any other application wherein the implant is deployed between two surfaces of tissues, and wherein the implant and the tissues define a closed, or near closed, volume into which a material (a structure filler, a medicament or a surgical tool) may be introduced, also fall within the scope of the present invention.

Advantageously, intervertebral implants described above may be implanted through an elongated conduit acting as a working channel.

Another advantage of the intervertebral implants and delivery system described above is that the elongated conduit working channel and the access channel to the implant's enclosed volume allow injection of bone particles to the evacuated disc volume.

In summary, intervertebral implants and delivery system described above improve the prior art spine implants and delivery systems by introducing implants that are inserted in a straight configuration and fold inside the evacuated disc volume to their closed loop configuration. The elongated conduit working channel enables the surgeon to perform the clinical operations needed for successful fusion of vertebrae including: (a) insertion of surgical tools to the implant's enclosed volume for evacuation of tissues and fluids from the formed disc volume and for preparation of the vertebrae end plates for bone injection, (b) implantation and deflection of the implants to their closed loop configuration, (c) injection of bone particles that fill the implant enclosed volume fully, and (d) insertion of imaging systems into the implant enclosed volume.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

What is claimed is:

1. A method for deploying an implant within a body comprising the steps of:
   (a) providing:
      (i) an elongated implant configured for forming a partial loop within the body and straightenable for delivery into the body along a guide, and
      (ii) an elongated tensing element linked to a distal portion of the elongated implant, the tensing element comprising a flat strip;
   (b) introducing the elongated implant along the guide into the body and applying tension to the tensing element continuously while said elongated implant is advanced beyond the guide so that the elongated implant deflects to form the partial loop on leaving the guide,
   wherein, for at least part of said introducing, advancing of the elongated implant is accompanied by retraction of at least part of the tensing element so that the distal portion of the elongated implant is drawn towards a proximal portion of the elongated implant,
   and wherein, in a final deployed form of the elongated implant, said elongated implant forms the partial loop with a gap between the distal portion and the proximal portion, and wherein a part of the tensing element remains as a bridging element bridging said gap between the distal portion and the proximal portion of the elongated implant, whereby the elongated implant and the bridging element form a closed loop, and wherein the closed loop formed by the elongated implant and the bridging element encloses an unobstructed central void, and wherein the unobstructed central void extends across a majority of a maximum external dimension of the closed loop in a plane of the closed loop.

2. The method of claim 1, wherein the elongated tensing element is threaded through an opening formed in the proximal portion of the elongated implant.

3. The method of claim 1, wherein the elongated tensing element is implemented as a spring element.

4. The method of claim 1, wherein the elongated implant comprises at least two sequential segments interconnected at an effective hinge, and wherein said continuously applied tension is effective to deflect at least a first of said sequential segments about said effective hinge as said first segment leaves the guide.

5. The method of claim 1, wherein the elongated implant is delivered to an intervertebral space as part of a vertebral fusion procedure.

6. The method of claim 1, wherein the guide is implemented as a conduit.

7. The method of claim 6, further comprising, prior to said introducing, inserting a surgical tool through the conduit to perform a surgical procedure on a target volume, wherein the surgical tool interacts with the conduit to define the target volume relative to a conduit position, said target volume being located laterally relative to a length of said conduit.

8. The method of claim 1, wherein, for at least part of said introducing, advancing of the elongated implant is accompanied by retraction of at least part of the tensing element relative to the guide.

9. The method of claim 1, further comprising, after formation of the closed loop, filling the unobstructed central void with bone particles or bone substitute.

10. The method of claim 1, further comprising, after formation of the closed loop, filling the unobstructed central void with a biocompatible material.

* * * * *